US00PP23014P3

(12) United States Plant Patent
Blom

(10) Patent No.: US PP23,014 P3
(45) Date of Patent: Sep. 4, 2012

(54) ***CHRYSANTHEMUM* PLANT NAMED 'ZANMUBEDAZ'**

(50) Latin Name: *Chrysanthemum×morifolium*
Varietal Denomination: Zanmubedaz

(75) Inventor: Wilhelmus Bernardus Blom, Leimuiden (NL)

(73) Assignee: Chrysanthemum Breeders Association Research B.V., Valkenburg Z-H (NL)

( * ) Notice: Subject to any disclaimer, the term of this patent is extended or adjusted under 35 U.S.C. 154(b) by 13 days.

(21) Appl. No.: 12/926,544

(22) Filed: Nov. 24, 2010

(65) Prior Publication Data
US 2012/0131711 P1 May 24, 2012

(51) Int. Cl.
*A01H 5/00* (2006.01)

(52) U.S. Cl. ..... Plt./296

(58) Field of Classification Search ..... Plt./296
See application file for complete search history.

*Primary Examiner* — Susan McCormick Ewoldt
(74) *Attorney, Agent, or Firm* — Steptoe & Johnson LLP

(57) ABSTRACT

A *chrysanthemum* plant named 'Zanmubedaz' characterized by its medium sized blooms with bronze ray floret with a dark center and prolific branching; natural season flower date September 21 (week 39) blooming for a period of 5 weeks.

3 Drawing Sheets

Botanical designation: *Chrysanthemum×morifolium* Ramat.

Cultivar denomination: 'Zanmubedaz'.

BACKGROUND OF THE INVENTION

The present invention relates to a new and distinct cultivar of *chrysanthemum* plant, botanically known as *Chrysanthemum×morifolium* Ramat., commercially known as a garden mum, and hereinafter referred to by the cultivar denomination 'Zanmubedaz'. 'Zanmubedaz' is a product of a breeding and selection program for outdoor pot mums (garden mums) which had the objective of creating new cultivars with a double type inflorescence, a natural season flower date around September 21-26 (week 39), blooming for a period of 5 weeks. 'Zanmubedaz' is a seedling resulting from a cross of the female parent i.d. 17747 with the male parent i.d.44758. Plants of the new cultivar 'Zanmubedaz' differ from plants of the female parent in the color of the ray-florets. The ray-florets of the seedling are bronze colored, while those of the female parent are red. Plants of the new cultivar 'Zanmubedaz' differ from plants of the male parent in the following characteristics. (1) Color ray-florets. And (2) Inflorescence size. (1) The color of the ray-florets of the seedling is bronze, while that of the male parent is pink. (2) The inflorescences of the seedling are smaller than those of the male parent.

The new and distinct cultivar was discovered and selected as a flowering plant by Wilhelmus Bernardus Blom on a cultivated field in Rijsenhout, The Netherlands in 2005. The first act of asexual production of 'Zanmubedaz' was accomplished when vegetative cuttings from the initial selection in 2005 were propagated further in a controlled environment in Rijsenhout, The Netherlands. The new cultivar has been found to retain its distinctive characteristics through successive propagations.

BRIEF DESCRIPTION OF THE DRAWINGS

The present invention of a new and distinct variety of *chrysanthemum* is shown in the accompanying drawings, the color being as nearly true as possible with color photographs of this type.

DESCRIPTION OF THE INVENTION

Figure 1:
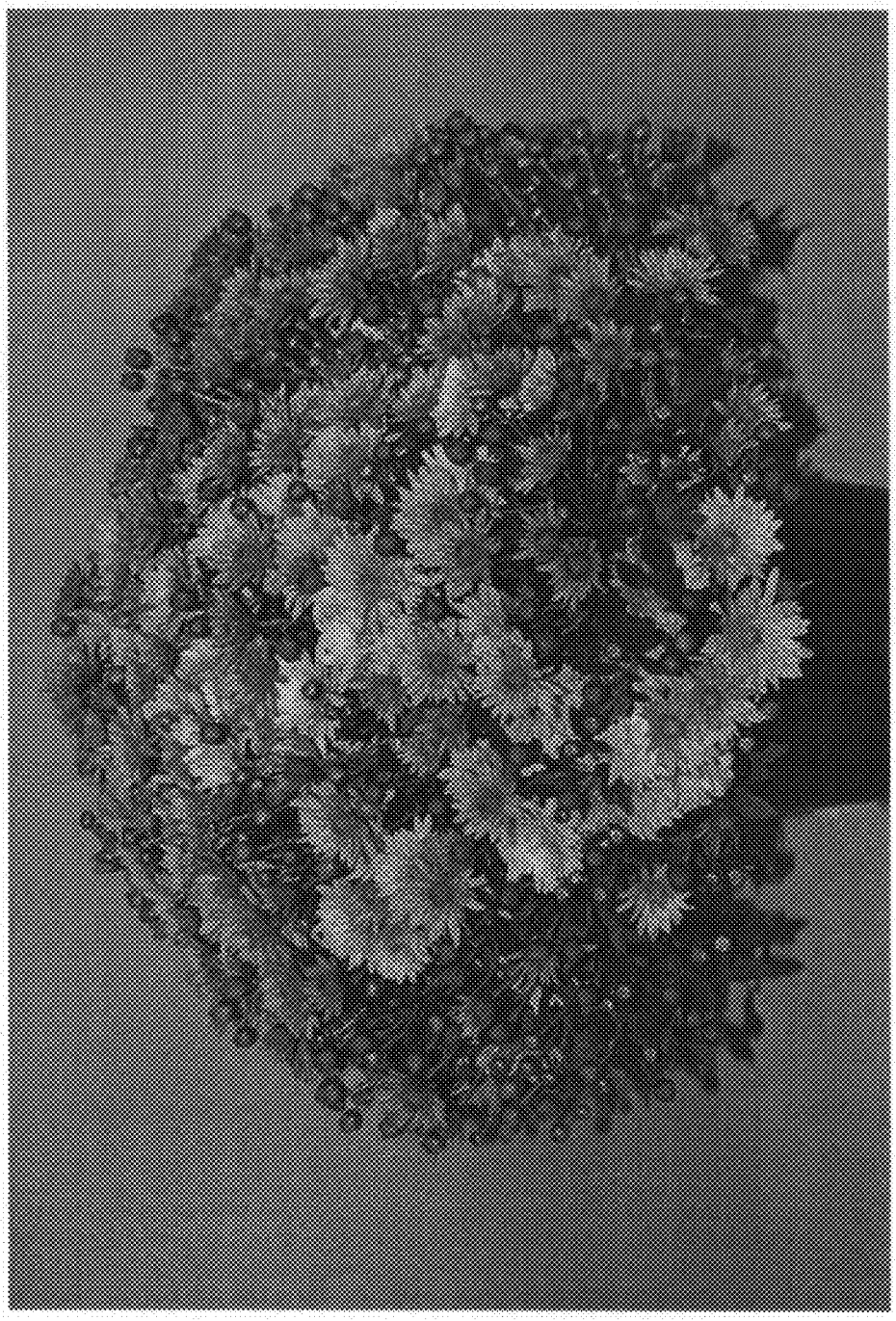
FIG. 1 shows a plant of the cultivar in full bloom.
Figure 2:
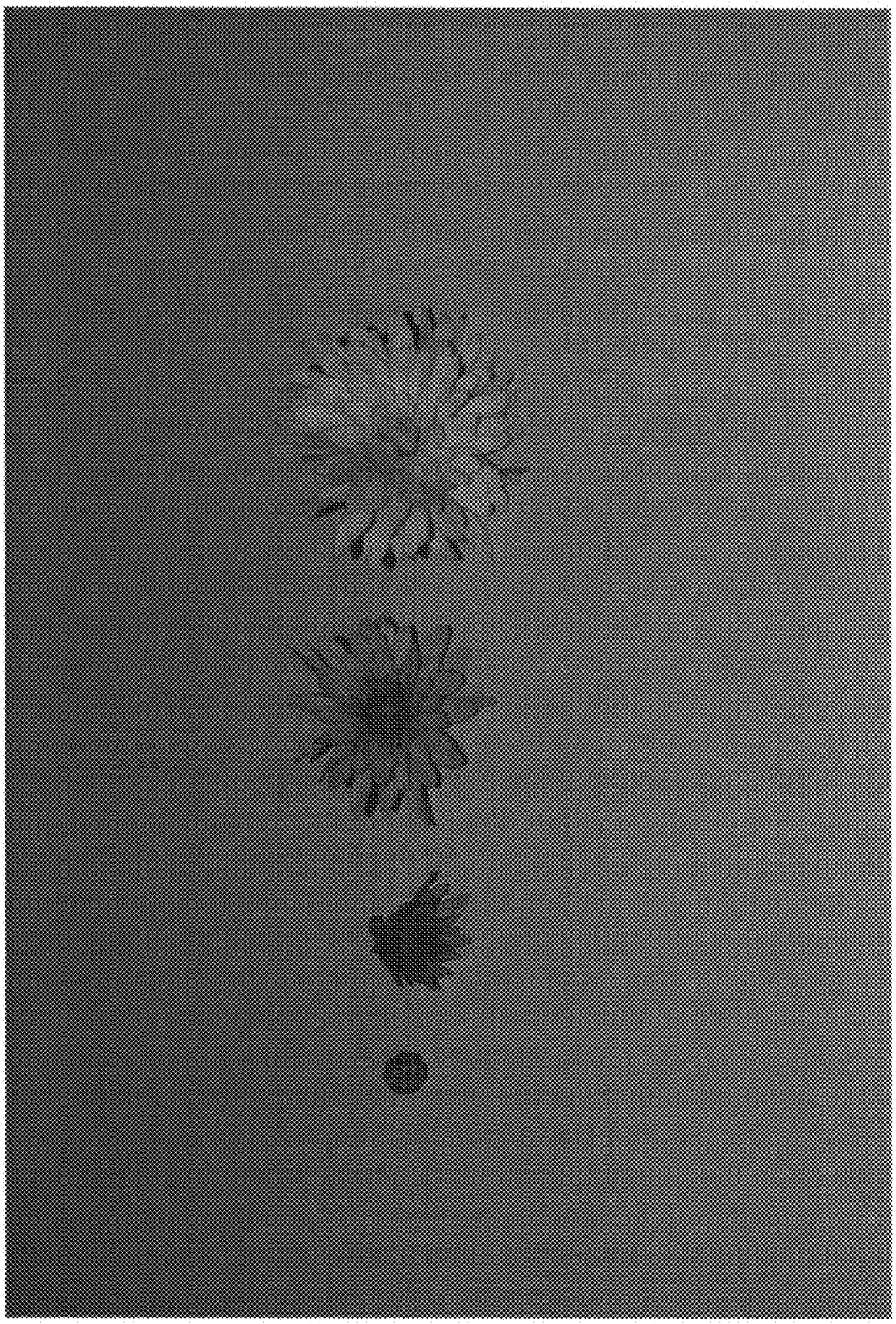
FIG. 2 shows the various stages of bloom of the new cultivar.
Figure 3:
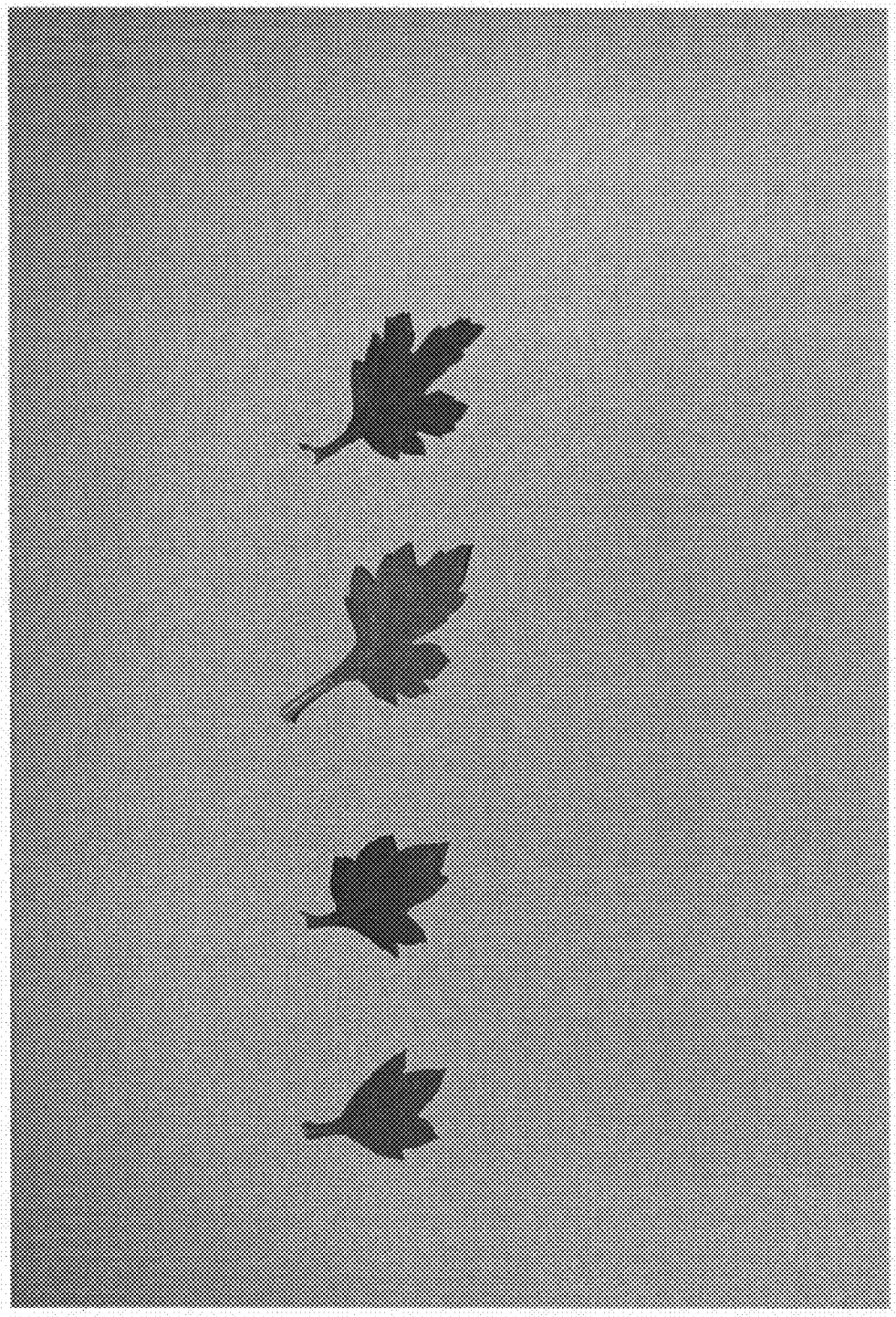
FIG. 3 shows the various stages of foliage of the new cultivar.

The observations and measurements were gathered from plants grown out door in Rijsenhout, The Netherlands under natural day length and temperature and planted in week 23 in 2009. The natural blooming date of this crop was September 21 (week 39) . The average height of the plants was 24 cm. No growth retardants were used. No tests were done on disease or insect resistance or susceptibility. No tests were done on cold or drought tolerance. This new variety produces medium sized blooms with bronze ray florets with a dark center, blooming for a period of 5 weeks.

From the cultivars known to inventor the most similar existing cultivar in comparison to 'Zanmubedaz' is 'Katelli' (U.S. Plant Pat. No. 16,674). When 'Katelli' and 'Zanmubedaz' are being compared the following difference is noticed: The differences of 'Katelli' and 'Zanmubedaz' are (1) Natural season blooming date. And (2) Plant size. (1) The plants of 'Zanmubedaz' flower later than those of 'Katelli'. (2) The plants of 'Zanmubedaz' are smaller than those of 'Katelli'.

The following is a description of the plant and characteristics that distinguish 'Zanmubedaz' as a new and distinct variety.

The color designations are taken from the plant itself. Accordingly, any discrepancies between the color designations and the colors depicted in the photographs are due to photographic tolerances. The color chart used in this description is: The Royal Horticultural Society Colour Chart, edition 2001.

TABLE 1

Botanical Description of *Chrysanthemum xmorifolium* Ramat. 'Zanmubedaz'

| | |
|---|---|
| **Bud** | |
| Size | Small; cross-section 5 mm, height 5 mm |
| Shape | Round |
| Texture | Pubescent |
| Outside Color | Greyed-green 191A |
| **Phyllaries** | |
| Number | 24-26, arranged in 3 rows |
| Shape | Elliptic |
| Apex | Acute |
| Base | Truncate |
| Margin | Entire |
| Color | Upper surface: Greyed-green 191B |
| Length and width | 4-5 mm; 2 mm |
| Texture | Pubescent |
| **Inflorescence** | |
| Type | Double |
| Height | 2 cm |
| Diameter | 5 cm |
| Peduncle length | 6-7 cm |
| Peduncle color | Green 138B |
| Peduncle diameter | 1.8 mm |
| Peduncle texture | Pubescent |
| Number per branch | Approx. 8-9 inflorescences |
| Duration of flowering | 5 weeks |
| Seeds | Produced in small quantities, ovate, Greyed-brown 199A, length 1.5 mm, diameter 0.5 mm |
| Fragrance | Faint chrysanthemum odor |
| **Color** | |
| Center of inflorescence | Immature stage: Greyed Orange 172A<br>Mature stage: Greyed Orange 172A |
| Color of upper surface of the ray-florets | Greyed Orange 163C |
| Color of the lower surface of the ray-florets | Greyed Orange 163B |
| Tonality from Distance | A garden mum with bronze flowers and a dark center |
| Color of the ray-florets after aging of the plant | Yellow Orange 17D |
| **Ray florets** | |
| Texture | Upper and lower surface smooth |
| Number | Ca. 210 |
| Shape | Narrowly elliptic |
| Apex | Rounded |
| Base | Attenuate |
| Cross-section | Convex |
| Longitudinal axis of majority | Straight to reflexing |
| Length of corolla tube | 3-5 mm |
| Ray-floret margin | Entire |
| Ray-floret length | 2-2.5 cm |
| Ray-floret width | 2-4 mm |
| Ratio length/width | High |
| Disc florets | Absent |
| **Receptacle** | |
| Color | Yellow-green 145D |
| Shape | Domed raised |
| Height | 5 mm |
| Diameter | 3 mm |

TABLE 1-continued

Botanical Description of *Chrysanthemum xmorifolium* Ramat. 'Zanmubedaz'

| | |
|---|---|
| **Reproductive Organs** | |
| Androecium | Absent |
| Pollen | Not produced |
| Gynoecium | Present on ray florets |
| Style color | Yellow-green 154C |
| Style Length | 3 mm |
| Stigma color | Yellow 7A |
| Stigma Width | 1 mm |
| Ovary | Enclosed in calyx |
| **Plant** | |
| Form | Grown as a spray type pot mum, outdoor raised and mounded |
| Growth habit | Spherical shape |
| Growth rate | Medium |
| Height | 24 cm |
| Width | 44 cm |
| Stem Color | Greyed-brown 199A |
| Stem Strength | Medium |
| Stem Brittleness | Brittle |
| Stem Anthocyanin Coloration | Not observed |
| Internode length | 2 cm |
| Length of lateral branch | From top to bottom 15 cm |
| Lateral branch color | Green 137 C |
| Lateral branch, attachment | Weak |
| Lateral branch diameter | 2 mm |
| Branching (average number of lateral branches) | Prolific with 8 breaks after pinching |
| Natural season blooming date | September 21 (week 39) |
| **Foliage** | |
| Leaf color | Upper side: Green 136B<br>Lower side: Green 138B |
| Color midvein | Upper side: Yellow-green 147D<br>Lower side: Yellow-green 148D |
| Size | Small; length 3-4 cm, width 1.5-2 cm |
| Quantity (number per lateral branch) | Ca. 15 |
| Shape | Broadly elliptic |
| Texture upper side | Sparsely pubescent |
| Texture under side | Pubescent |
| Venation arrangement | Palmate |
| Shape of the margin | Serrated |
| Shape of Base of Sinus Between Lateral Lobes | Rounded |
| Margin of Sinus Between Lateral Lobes | Diverging |
| Shape of Base | Attenuate to Truncate |
| Apex | Mucronulate |
| Petiole length | 0.5-1.5 cm |
| Petiole diameter | 2 mm |
| Petiole color | Yellow-green 147D |

TABLE 2

Differences with the comparison variety (when grown side to side)

| | "Zanmubedaz" | 'Katelli' |
|---|---|---|
| Natural season flowering date | Week 39 | Week 37 |
| Plant height | 24 cm | 30 cm |

I claim:

1. A new and distinct *chrysanthemum* plant named 'Zanmubedaz' as described and illustrated.

* * * * *